United States Patent [19]

Colin et al.

[11] Patent Number: 4,857,653
[45] Date of Patent: Aug. 15, 1989

[54] PROCESS FOR THE PREPARATION OF TAXOL AND 10-DEACETYLTAXOL

[75] Inventors: Michel Colin, Thoiry; Daniel Guenard, Montrouge; Francoise Gueritte-Voegelein; Pierre Potier, both of Paris, all of France

[73] Assignee: Rhone-Poulenc Sante, Courbevoie, France

[21] Appl. No.: 73,154

[22] Filed: Jul. 14, 1987

[30] Foreign Application Priority Data

Jul. 17, 1986 [FR] France ................................ 86 10401

[51] Int. Cl.$^4$ ........................................... C07D 505/14
[52] U.S. Cl. .................................... 549/511; 549/510
[58] Field of Search ................................ 549/510, 511

[56] References Cited

PUBLICATIONS

V. Senilh et al., C.R. Acad.Sc. Paris, t. 299, Serie II, No. 15 (1984), pp. 1039–1043.
M. E. Jung et al., Jour.Chem.Soc., Chem.Comm. (1978), pp. 315–316.
R. S. Lott et al., Jour.Chem.Soc., Chem.Comm. (1979), pp. 495–496.
E. Herranz et al., Jour.Am.Chem.Soc., vol. 100:11 (1978), pp. 3596–3598.

Theodora W. Greene, Protective Groups in Organic Synthesis, (1981), pp. 223–225 and 232.

*Primary Examiner*—Glennon H. Hollrah
*Assistant Examiner*—Mark W. Russell
*Attorney, Agent, or Firm*—Stevens, Davis, Miller & Mosher

[57] ABSTRACT

Taxol and 10-deacetyltaxol are prepared from a compound of formula:

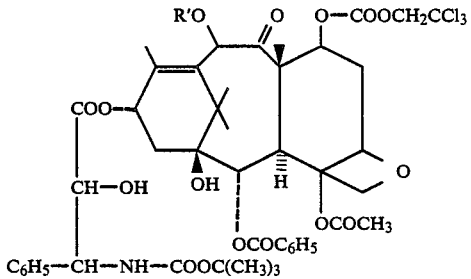

in which R′ represents acetyl or 2,2,2-trichloroethoxycarbonyl radical, by removal of the t-butoxycarbonyl radical, benzoylation of the amine product obtained, and removal of the 2,2,2-trichloroethoxycarbonyl group(s).

4 Claims, No Drawings

PROCESS FOR THE PREPARATION OF TAXOL AND 10-DEACETYLTAXOL

The present invention relates to the preparation of taxol and 10-deacetyltaxol from baccatin III and 10-deacetylbaccatin III respectively.

Among taxan derivatives of general formula:

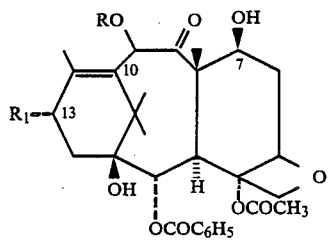

taxol is that in which R represents acetyl and $R_1$ represents a $(2'R,3'S)$-$[$—OCO—CHOH—CH($C_6H_5$)NH—CO$C_6H_5]$ radical, 10-deacetyltaxol is that in which R represents hydrogen and $R_1$ represents a $(2'R,3'S)$-$[$—OCO—CHOH—CH($C_6H_5$)NHCO$C_6H_5]$ radical, baccatin III is that in which R represents an acetyl radical and $R_1$ represents a hydroxy radical, and 10-deacetylbaccatin III is that in which R represents a hydrogen atom and $R_1$ represents a hydroxy radical.

Taxol, 10-deacetyltaxol and baccatin III can be extracted with some difficulty from the trunk bark of different species of Taxus (yew) and the yields are generally low, of the order of 100 mg/kg in the case of taxol. However baccatin III is present in relatively large quantities in the wood.

10-Deacetylbaccatin III is extracted much more easily and with better yields (300 mg/kg of leaves) from yew leaves.

Whereas taxol and 10-deacetyltaxol are known to promote in vitro the polymerization of tubulin and to inhibit, at the same time, the depolymerization of microtubules induced by cold or by calcium ions, baccatin III and 10-deacetylbaccatin III only show these properties feebly and do not therefore constitute antitumour agents which can be used therapeutically.

The present invention provides a process for converting baccatin III and 10-deacetylbaccatin III into taxol and 10-deacetyltaxol respectively, which have remarkable antitumour properties.

The conversion of baccatin III or 10-deacetylbaccatin III into the product of general formula:

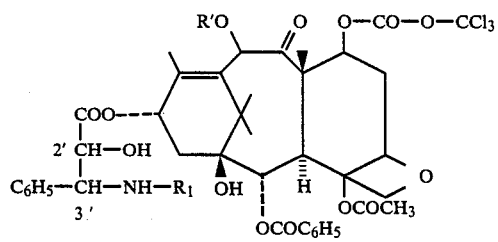

in which R' represents an acetyl or 2,2,2-trichloroethoxycarbonyl radical and $R_1$ represents an ethoxycarbonyl or paratoluenesulphonyl radical, is known, especially from V. Senilh et al., C.R. Acad. Sci. Paris, 299, series II, no. 15, 1039–1043 (1984). However, considering the complexity and the fragility of these products, it has not been possible until now to replace the substituent $R_1$ with the benzoyl radical present in taxol and 10-deacetyltaxol.

The process of the present invention for the preparation of taxol or 10-deacetyltaxol and their 2'S, 3'R isomers comprises reacting halotrialkylsilane with a compound of formula:

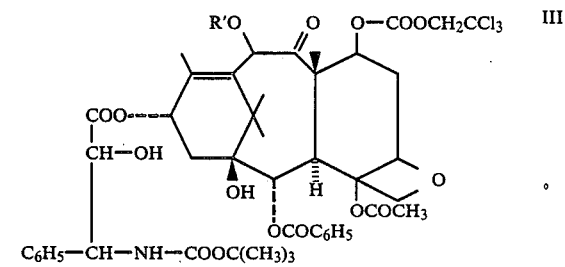

in which R' represents acetyl or 2,2,2-trichloroethoxycarbonyl, in an organic solvent to produce a product of formula:

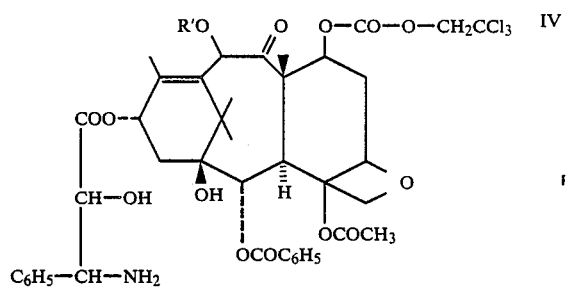

in which R' is defined above, and reacting the said product with benzoyl chloride in the presence of an acid acceptor to produce a product of formula:

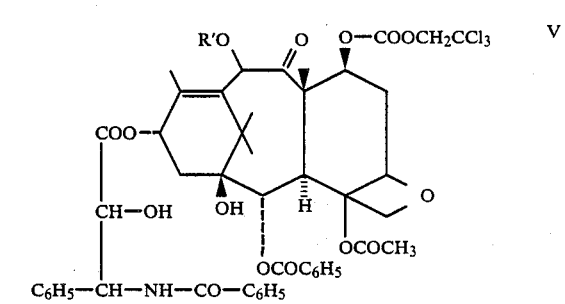

in which R' is as defined above, and then reacting this product with zinc in acetic acid to produce taxol (when R' in the starting material is 2,2,2-trichloroethoxycarbonyl).

The invention is based in part on the discovery that the compounds of formula III can be converted into products of formula IV in which R' is defined above, by reaction with a halotrialkylsilane such as iodotrimethylsilane, operating in an organic solvent such as acetonitrile at a temperature in the vicinity of 0° C.

The product of formula IV is then converted into a product of formula V in which R' is as defined above, by reacting with benzoyl chloride at a temperature in the vicinity of 20° C. and in the presence of an acceptor for acid such as pyridine.

The product of general formula V is converted into taxol or into 10-deacetyltaxol by replacing the 2,2,2-trichloroethoxycarbonyl radical(s) with a hydrogen atom, e.g. using zinc in the presence of acetic acid.

Taxol and 10-deacetyltaxol obtained by the process of the present invention may be purified by physicochemical methods such as chromatography.

The starting material of formula III exists in the form of stereoisomers (2'S,3'R and 2'R,3'S) from which taxol (2'R,3'S), 10-deacetyltaxol (2'R,3'S) and the 2'S,3'R isomers of taxol and 10-deacetyltaxol may be prepared.

The following Example illustrates the invention.

EXAMPLE 1

Iodotrimethylsilane (0.025 cc) is added, under an argon atmosphere and at a temperature of 0° C. to a solution of the product of formula III (170 mg) in which R' represents a 2,2,2-trichloroethoxycarbonyl radical, in acetonitrile (5 cc). When the starting material has disappeared, methanol is added and the mixture is concentrated to dryness. The residue obtained is purified by silica thick layer chromatography, eluting with a methylene chloride:methanol (95:5 by volume) mixture. The product of formula IV in which R' represents a 2,2,2-trichloroethoxycarbonyl radical, with the following characteristics, is thereby obtained (yield=75%):

infrared spectrum: characteristic absorption bands at 3670, 3500, 3400, 2950, 1765 and 1735 cm$^{-1}$ and proton nuclear magnetic resonance spectrum (CDCl$_3$, 200 MHz, shifts in ppm): 1.18 (s, 3H): 1.25 (s, 3H); 1.85 (s, 3H), 2.01 (s, 3H); 2.31 (s, 3H); 2.56 (m, 1H); 3.89 (d, J=7, 1H); 4.16 and 4.34 (2d, J=9, 2H); 4.41 (broad s, 2H); 4.63 and 4.94 (2d, J=12, 2H); 4.81 (s, 2H); 4.96 (d, J=9, 1H); 5.58 (m, 1H); 5.69 (d, J=7, 1H); 6.19 (t, J=9, 1H); 6.28 (s, 1H); 7.47 (5H); 7.57, 7.69 and 8.18 (5H).

Benzoyl chloride (1 equivalent) is added to a solution of the product obtained above (30 mg) in pyridine (2 cc). The reaction mixture is stirred at ambient temperature until the starting material has disappeared. After hydrolysis, extraction is carried out with methylene chloride. After drying, filtering and evaporating off the solvent, the product of formula V in which R' represents a 2,2,2-trichloroethoxycarbonyl radical, with the following characteristics, is obtained in a quantitative yield:

infrared spectrum: characteristic absorption bands at 3560, 2440, 2950, 1765, 1740, 1730, and 1665 cm$^{-1}$ and proton nuclear magnetic resonance spectrum (CDCl$_3$, 200 MHz, shifts in ppm): 1.19 (s, 3H); 1.26 (s, 3H); 1.88 (s, 3H); 1.90 (s, 3H); 2.42 (s, 3H); 3.93 (d, J=7, 1H); 4.23 and 4.27 (2d, J=9, 2H); 4.63 and 4.94 (2d, J=12, 2H); 4.80 (s, 2H); 4.83 (d, J=2, 1H); 4.99 (d, J=9, 1H); 5.58 (m, 1H); 5.75 (d, J=7, 1H); 5.84 (dd, J=9 and J=2, 1H); 6.28 (s and t, 2H); 7.09 (d, J=9, 1H); 7.41–8.17 (15H).

The product obtained above is dissolved in acetic acid and zinc powder is added. The reaction mixture is stirred for 2 hours at 50° C. and then filtered and concentrated to dryness. The residue is taken up with water and then extracted with ethyl acetate. The organic phases are concentrated to dryness. 10-Deacetyltaxol, the characteristics of which are identical to those described in the literature. [V. Senilh et al., J. Nat. Prod, 47, 131–137 (1984)] is thereby obtained (yield=90%).

The starting material of formula III in which R' represents a 2,2,2-trichloroethoxycarbonyl radical may be prepared as follows:

A solution of tert-butyl N-chlorocarbamate sodium salt (0.5 g) and silver nitrate (1 g) in acetonitrile (20 cc) is stirred vigorously for 5 minutes. A solution (0.2 cc) of osmium tetroxide in tert-butyl alcohol (0.1 mol per liter solution), the product of formula:

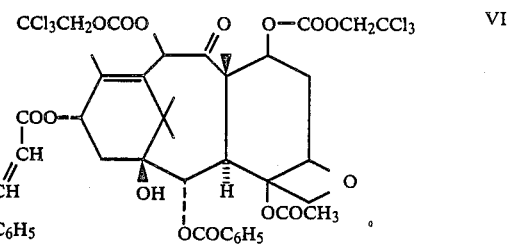

(2 g) and water (0.16 cc) are then added. After stirring for 20 hours at a temperature in the vicinity of 20° C. and in the absence of light, tert-butyl N-chlorocarbamate sodium salt (0.5 g), osmium tetroxide solution (0.1 cc) and water (0.06 cc) are added. After stirring vigorously for 48 hours, the reaction mixture is filtered through Celite. The filter is rinsed with acetonitrile and the filtrate is concentrated to dryness. The product obtained is purified by chromatography on silica (Merck 7736 silica), eluting with an ether:hexane (50:50 by volume) mixture and operating under a slight pressure. The unreacted product of formula VI (900 mg) and the oxyaminated products are purified and separated by thick layer chromatography, eluting with a methylene chloride:methanol (98:2 by volume) mixture.

The following are thereby obtained:

(1) The product (2'R,3'S) of general formula III (295 mg) in which R' represents a 2,2,2-trichloroethoxycarbonyl radical, the characteristics of which are as follows:

specific rotation: $[\alpha]_D^{23} = -38.4°$ (c=1, chloroform)

ultraviolet spectrum:
λmax=231 nm (15150)
λmax=275 nm (1200)
λmax=283 nm (1035)

infrared spectrum: main characteristic absorption bands at 3580, 3440, 2960, 1770, and 1730 cm$^{-1}$ proton nuclear magnetic resonance spectrum (CDCL$_3$; 400 MHz; shifts in ppm): 1.21 (s, 3H); 1.27 (s, 3H); 1.36 (s, 9h); 1.86 (s, 3H); 1.96 (s, 3H); 2.39 (s, 3H); 2.62 (m, 1H); 3.90 (d, J=7, 1H); 4.17 and 4.32 (2d, J=9, 2H); 4.63 (d, J=3, 1H); 4.59 and 4.90 (2d, J=12, 2H); 4.77 (s, 2H); 4.96 (d, J=9, 1H); 5.27 (dd, J=9 and J=3, 1H); 5.42 (d, J=9, 1H); 5.55 (m, 1H); 5.69 (d, J=7, 1H); 6.21 (t, J=9, 1H); 6.23 (s, 1H); 7.39 (5H); 7.51, 7.62 and 8.09 (5H); and (2) the product (2'S,3'R) of formula III (250 mg) in which R' represents a 2,2,2-trichloroethoxycarbonyl radical, the characteristics of which are as follows:

specific rotation: $[\alpha]_D^{23} = -43.5°$ (c=1, chloroform)

ultraviolet spectrum:
λmax=231 nm (15300)
λmax=275 nm (1035)
λmax=283 nm (905)

infrared spectrum: characteristic absorption bands at 3400, 3000, 1770 and 1730 cm$^{-1}$ proton nuclear magnetic resonance spectrum (CDCl$_3$, 400 MHz, shifts in ppm): 1.18 (s, 3H); 1.23 (s, 3H); 1.40 (s, 9H); 1.86 (s, 3H); 2.08 (s, 3H); 2.24 (s, 3H); 2.64 (m, 1H); 3.94 (d, J=7, 1H); 4.17 and 4.32 (d, J=9, 2H); 4.48 (d, J=3, 1H); 4.60 and 4.92 (2d, J=12, 2H); 4.78 (s, 2H); 4.97 (d, J=9, 1H); 5.22 (dd, J=9 and J=3, 1H); 5.32 (d, J=9, 1H); 5.58 (m, 1H); 5.70 (d, J=7, 1H); 6.07 (t, J=9, 1H); 6.27 (s, 1H); 7.33–7.45 (5H); 7.48, 7.61 and 8.04 (5H).

The starting material for formula VI may be prepared by one of the following methods:

(1) Oxalyl chloride (11.92 cc) is added to a solution of cinnamic acid (9.84 g; 66.5 mmol) in anhydrous toluene (150 cc). The reaction mixture is stirred for 1 hour at 60° C. and the excess oxalyl chloride is removed by distillation. The cinnamoyl chloride obtained is taken up with anhydrous toluene (300 cc) and the product of formula:

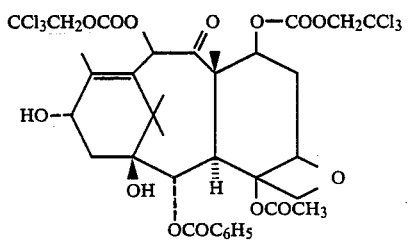

(12 g) and silver cyanide (7.9 g) are then added. The reaction mixture is heated for 10 hours at 110° C., with vigorous stirring. After cooling, the reaction mixture is filtered and the precipitate is rinsed with ethyl acetate. The combined filtrates are poured into ice-cold water. Extraction is carried out with ethyl acetate. The combined organic phases are concentrated to dryness and then taken up with ether (200 cc). A stream of ammonia is passed through this solution until the ammonium cinnamate formed precipitates. After filtering, the ethereal solution is concentrated and the residue is chromatographed on silica (Merck 7736 silica), eluting with methylene chloride under pressure. The product of formula VI (7.6 g), with the following characteristics, is thereby obtained (yield=55%):

$[\alpha]_D = -56°$ (c=0.567; chloroform)

ultraviolet spectrum:
  $\lambda$max=217 nm (26800)
  $\lambda$max=222 nm (26900)
  $\lambda$max=232 nm (16100)
  $\lambda$max=276 nm (23600)
  $\lambda$max=283 nm (24400)

infrared spectrum: main characteristic absorption bands at 3420, 1760, 1725, 1710 and 1635 cm$^{-1}$ proton nuclear magnetic resonance spectrum (CDCl$_3$; shifts in ppm): 5.73 (d, J=7, C$_2$H); 3.99 (d, J=7, C$_3$H); 5.02 (d, J=9, C$_5$H); 1.88 and 2.68 (m, 2×C$_6$H); 5.62 (m, C$_7$H); 6.30 (s, C$_{10}$H); 6.21 (t, J=8, C$_{13}$H); 2.48 (m, C$_{14}$H$_2$); 19.2 (s, C$_{16}$H$_3$); 1.23 (s, C$_{17}$H$_3$); 2.16 (s, C$_{18}$H$_3$); 1.88 (s, C$_{19}$H$_3$); 4.20 and 4.34 (d, J=9, 2×C$_{20}$H); 2.31 (acetate); 7.45, 7.60 and 8.07 (benzoate); 6.53 (d, J=16, C$_2$'H); 7.89 (d, J=16, C$_3$'H); 7.45 (4H); 7.60 (1H); 4.62 to 4.93 (d, J=12); 4.79 (s, 2H)

mass spectrum (chemical ionization): m/z 1023 (MH$^+$), 1005, 831, 813, 683, 665, 491, 431, 369, 309, 291, 149, 131 and 123.

(2) Cinnamic acid (35.52 g; 240 mmols), anhydrous toluene (1 liter), dicyclohexylcarbodiimide (49.44 g; 240 mmols), product of formula VII (53.5 g; 60 mmols) and dimethylaminopyridine (7.32 g; 60 mmols) are introduced into a 2 liter three-necked round-bottomed flask, equipped with a stirrer and a thermometer, under an argon atmosphere. The mixture is heated for 18 hours at 70° C. under an argon atmosphere. After cooling at 0° C. for 4 hours, the precipitate formed is separated by filtration and then washed with cold toluene (100 cc).

The filtrate is concentrated to dryness and then taken up with methylene chloride (1 liter). The solution in methylene chloride is washed with an aqueous 3% (w/v) hydrochloric acid solution (3×150 cc). After concentrating the organic phase, the residue (92 g) is taken up with ethyl ether (500 cc). The solution is allowed to stand at a temperature in the vicinity of 0° C. for 48 hours. The precipitate formed is separated by filtration and washed with ethyl ether at 0° C. The filtrate is concentrated to dryness. A product (89 g) is thereby obtained, which is chromatographed on Merck 7734 silica (2.7 kg), eluting with a toluene:methanol (95:5 by volume) mixture. The product of formula VI (58 g) is thereby obtained (yield=94.6%).

The starting material of formula VII may be prepared as follows:

A solution of 10-deacetylbaccatin III (30 g; 55 mmol) in anhydrous pyridine (480 cc) is cooled to 3° C. under an argon atmosphere. 2,2,2-Trichloroethyl chloroformate (25.5 cc; 184 mmol) is added in the course of 3 minutes. The reaction mixture is stirred for 3 minutes at 20° C. and then for 6 minutes at 28° C. The solution is then cooled with an ice bath and quickly poured into ice-cold water (1 liter). The aqueous phase is extracted 3 times with methylene chloride (1 liter in total). After concentration, the pyridine is removed by exhaustive extraction with 1,2-dichloroethane. The crude product obtained (61.9 g) is purified by chromatography on silica (Merck 7736 silica) (1.2 kg), eluting with a methylene chloride:methanol (99:1 by volume) mixture.

The product of formula VII (45.6 g), with the following characteristics, is thereby obtained (yield=93%):

melting point=233°–234° C.

specific rotation $[\alpha]_D^{23} = -58°$ (c=0.465, chloroform)

ultraviolet spectrum:
  $\lambda$max=232 nm (19000)
  $\lambda$max=276 nm (990)
  $\lambda$max=283 nm (810)

infrared spectrum: characteristic absorption bands at 3420, 1765, 1730 and 1720 cm$^{-1}$ proton nuclear magnetic resonance spectrum (CDCl$_3$, shifts in ppm): 1.12 (s, 3H); 1.16 (s, 3H); 1.85 (s, 3H); 2.16 (s, 3H); 2.30 (s, 3H); 2.30 (m, 2H); 2.05 and 2.65 (2m, 2H); 4.00 (d, J=7, 1H); 4.18 and 4.35 (2d, J=9, 2H); 4.63 and 4.92 (2d, J=12, 2H); 4.76 and 4.80 (2d, J=12, 2H); 4.92 (t, J=9, 1H); 5.00 (d, J=9, 1H); 5.61 (m, 1H); 5.66 (d, J=7, 1H); 6.30 (s, 1H); 7.50, 7.64 and 8.13 (2t and 1d, J=7, 5H)

mass spectrum (chemical ionization): m/z 893 (MH$^+$), 875, 701, 683, 579, 387, 327, 309 and 123.

The 10-deacetylbaccatin III may be obtained as follows:

Non-dried Taxus baccata L. leaves (100 kg) are ground and then subjected to accelerated percolation, using a rotary device, with 95° alcohol (the actual alcohol content of which changes to 80°-85° because of the water contained in the leaves). The first maceration is carried out with alcohol (300 liters) and the following macerations are carried out with alcohol (4×200 liters) recovered by distillation and the alcohol level of which is maintained at 85°. Each percolation lasts for 10 hours and is carried out at a temperature in the vicinity of 20° C. The mixing is ensured by circulating the solvent using a pump.

Each ethanolic phase is concentrated under reduced pressure (50-60 mm Hg; 5.4 kPa). The concentrates from each operation (approximately 70 liters), with high water contents, are combined and concentrated again to a volume of 20 liters so as to remove the residual alcohol.

The extract, which is not evaporated to dryness, remains in an aqueous medium (20 liters), in the form of a solid suspension. The suspension is taken up with methylene chloride (9 extractions with a total of 100 liters of methylene chloride).

The solution in methylene chloride thus obtained (87 liters), which contains the dry extract (2 kg), is concentrated to a volume of 5 liters.

Chromatography is carried out on a 24 cm diameter column containing silica (10.3 kg) (Zeosil: 8 kg; Celite: 2.3 kg).

Successive elutions are carried out, at a flow rate of 8 to 9 liters/hour, with:
methylene chloride (150 liters) (fraction 1);
a methylene chloride:methanol (99.5:0.5 by volume) mixture (150 liters) (fraction 2);
a methylene chloride:methanol (99:1 by volume) mixture (170 liters) (fraction 3) and
a methylene chloride:methanol (98:2 by volume) mixture (130 liters) (fraction 4).

The first two fractions combined together give 1.74 kg of dry extract. The third fraction gives 390 g of dry extract. The fourth fraction gives 20 g of dry extract.

The third fraction (390 g), which contains essentially the 10-deacetylbaccatin III, is chromatographed again on silica, eluting with a methylene chloride:methanol (99:1 by volume) mixture at a flow rate of 4 liters/hour. 4 fractions are thus obtained, the most useful of which (154 g) gives, after concentrating and digesting in methylene chloride, 22 g of pure 10-deacetylbaccatin III.

The mother liquors (132 g), purified by chromatography on silica, give 8 g of 10-deacetylbaccatin III.

The total yield is 300 mg of 10-deacetylbaccatin III per kg of leaves.

We claim:

1. A process for the preparation of taxol or 10-deacetyltaxol, and their 2'S, 3'R isomers which comprises reacting halotrialkylsilane with a compound of formula:

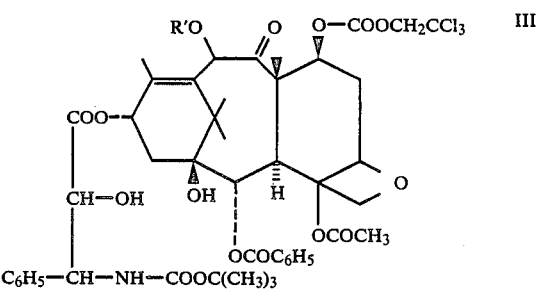

in which R' represents acetyl or 2,2,2-trichloroethoxycarbonyl, in an organic solvent at about 0° C. to produce a product of formula:

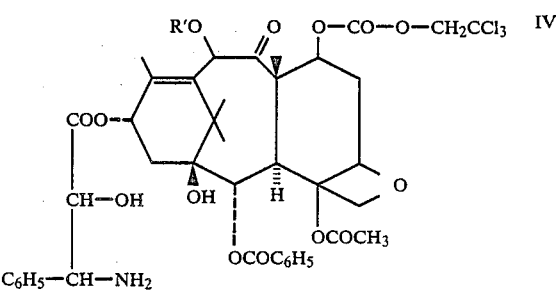

in which R' is as defined above, and reacting the said product with benzoyl chloride in the presence of an acid acceptor to produce a product of formula:

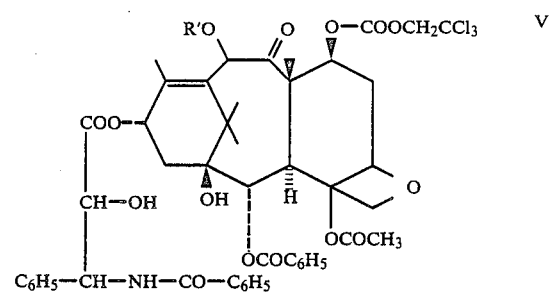

in which R' is as defined above, and then reacting this product with zinc in acetic acid to produce taxol, when R' in the starting material is acetyl, or 10-deacetyltaxol, when R' in the starting material is 2,2,2-trichloroethoxycarbonyl.

2. Process according to claim 1 in which the halotrialkylsilane is iodotrimethylsilane.

3. Process according to claim 1 in which the said organic solvent is acetonitrile.

4. Process according to claim 1 in which the said acid acceptor is pyridine used at a reaction temperature of about 20° C.

* * * * *